US006937323B2

(12) United States Patent
Worthington et al.

(10) Patent No.: US 6,937,323 B2
(45) Date of Patent: Aug. 30, 2005

(54) INTERACTIVE SYSTEM FOR ANALYZING BIOLOGICAL SAMPLES AND PROCESSING RELATED INFORMATION AND THE USE THEREOF

(75) Inventors: Mark Oscar Worthington, Irvine, CA (US); Jorma Antero Virtanen, Las Vegas, NV (US); Andrew Attila Pal, Ranch Santa Margarita, CA (US)

(73) Assignees: Burstein Technologies, Inc., Mission Viejo, CA (US); Nagaoka & Co. Ltd. (JP)

(*) Notice: Subject to any disclaimer, the term of this patent is extended or adjusted under 35 U.S.C. 154(b) by 91 days.

(21) Appl. No.: 09/986,078

(22) Filed: Nov. 7, 2001

(65) Prior Publication Data

US 2002/0118355 A1 Aug. 29, 2002

Related U.S. Application Data (60) Provisional application No. 60/246,824, filed on Nov. 8, 2000.

(51) Int. Cl.[7] ............................. G01N 21/00; G06F 7/00
(52) U.S. Cl. .......................................... 356/73; 700/215
(58) Field of Search .................. 356/73, 440, 244–246, 356/39–40, 436, 82.09, 82.05, 164, 165; 422/12.05, 82.05, 82.09, 82.04; 434/165, 809; 436/164, 165

(56) References Cited

U.S. PATENT DOCUMENTS

| | | |
|---|---|---|
| 3,555,284 A | 1/1971 | Norman |
| 3,736,432 A | 5/1973 | Sweet |
| 3,939,350 A | 2/1976 | Kronick et al. |
| 3,966,322 A | 6/1976 | Greaves et al. |
| 4,608,344 A | 8/1986 | Carter et al. |
| 4,743,558 A | 5/1988 | Guigan |
| 4,870,508 A | 9/1989 | Van Rosmalen et al. |

(Continued)

FOREIGN PATENT DOCUMENTS

| | | |
|---|---|---|
| EP | 0 392 475 | 10/1990 |
| EP | 0 417 305 A1 | 3/1991 |
| EP | 0 504 432 A1 | 9/1992 |
| EP | 0 521 421 A2 | 1/1993 |
| EP | 0 866 449 A2 | 9/1998 |
| WO | WO 96/09548 | 3/1996 |
| WO | WO 97/11460 | 3/1997 |
| WO | WO 98/01858 | 1/1998 |
| WO | WO 99/13388 | 3/1999 |
| WO | WO 99/32663 | 7/1999 |
| WO | WO 00/20838 | 4/2000 |
| WO | WO 00/26677 | 5/2000 |
| WO | WO 02/06836 A2 | 1/2002 |

OTHER PUBLICATIONS

Tibbe et al., "Optical Tracking and Detection of Immuno-magnetically Selected and Aligned Cells", Nature Biotechnology, vol. 17, Dec. 1999, pp. 1210–1213.

Baruch et al., *Computing & Controlling Engineering Journal*, Feb. 1996:39–45, 1996, "Remote control and robots: an Internet solution."

*Primary Examiner*—Michael P. Stafira
(74) *Attorney, Agent, or Firm*—Knobbe, Martens, Olson & Bear, LLP (57) ABSTRACT

A interactive system for chemical and biological testing with the instant data processing and information analysis capability. The system utilizes a specially designed bio-disc and an optical reader attached to a computer to deliver a wide range of tests, such as clinical laboratory diagnostic tests, biological warfare agent detection, forensic DNA tests, and food and water contamination tests, to a remote location. The test data are analyzed by a central data processing unit connected to the computer through a network, and the result is distributed to authorized users through the network. The interactive system also offer users enhanced information and additional relevant products at the point of need.

30 Claims, 8 Drawing Sheets

U.S. PATENT DOCUMENTS

| | | |
|---|---|---|
| 4,898,832 A | 2/1990 | Klose et al. |
| 4,917,865 A | 4/1990 | Romanauskas |
| 4,961,916 A | 10/1990 | Lesage et al. |
| 5,002,867 A | 3/1991 | Macevicz |
| 5,021,236 A | 6/1991 | Gries et al. |
| 5,087,556 A | 2/1992 | Ertinghausen |
| 5,112,134 A | 5/1992 | Chow et al. |
| 5,281,540 A | 1/1994 | Merkh et al. |
| 5,310,523 A | 5/1994 | Smethers et al. |
| 5,329,461 A | 7/1994 | Allen et al. |
| 5,407,554 A | 4/1995 | Saurer |
| 5,413,939 A | 5/1995 | Gustafson et al. |
| 5,424,036 A | 6/1995 | Ushikubo |
| 5,478,750 A | 12/1995 | Bernstein et al. |
| 5,488,567 A | 1/1996 | Allen et al. |
| 5,492,806 A | 2/1996 | Drmanac et al. |
| 5,566,159 A | 10/1996 | Shapira |
| 5,585,069 A | 12/1996 | Zanzucchi et al. |
| 5,598,393 A | 1/1997 | Alon et al. |
| 5,631,166 A | 5/1997 | Jewell |
| 5,631,844 A | 5/1997 | Margrey et al. |
| 5,684,774 A | 11/1997 | Yamamuro |
| 5,700,655 A | 12/1997 | Croteau et al. |
| 5,736,410 A | 4/1998 | Zarling et al. |
| 5,834,758 A | 11/1998 | Trulson et al. |
| 5,874,219 A | 2/1999 | Rava et al. |
| 5,922,591 A | 7/1999 | Anderson et al. |
| 5,930,033 A | 7/1999 | Inoue et al. |
| 5,995,209 A | 11/1999 | Ohman et al. |
| 6,024,883 A | 2/2000 | Jewell |
| 6,026,068 A | 2/2000 | Obata et al. |
| 6,084,843 A | 7/2000 | Abe et al. |
| 6,121,048 A | 9/2000 | Zaffaroni et al. |
| 6,147,943 A | 11/2000 | Ogasawara et al. |
| 6,192,320 B1 * | 2/2001 | Margrey et al. |
| 6,222,619 B1 | 4/2001 | Herron et al. |
| 6,225,625 B1 | 5/2001 | Pirrung et al. |
| 6,231,812 B1 * | 5/2001 | Rothberg et al. |
| 6,277,653 B1 | 8/2001 | Challener et al. |
| 6,309,601 B1 | 10/2001 | Juncosa et al. |
| 6,327,031 B1 * | 12/2001 | Gordon |
| 6,338,139 B1 | 1/2002 | Ando et al. |
| 6,339,473 B1 * | 1/2002 | Gordon |
| 6,387,331 B1 | 5/2002 | Hunter |
| 6,395,562 B1 | 5/2002 | Hammock et al. |
| 6,476,907 B1 * | 11/2002 | Gordon |
| 6,514,461 B1 * | 2/2003 | Lappe et al. |
| 6,560,546 B1 * | 5/2003 | Shenk et al. |
| 2001/0052976 A1 | 12/2001 | Juncosa et al. |
| 2002/0097658 A1 | 7/2002 | Worthington et al. |
| 2002/0098528 A1 | 7/2002 | Gordon et al. |
| 2002/0106786 A1 | 8/2002 | Carvalho et al. |
| 2002/0139936 A1 | 10/2002 | Dumas |
| 2002/0145960 A1 | 10/2002 | Worthington et al. |
| 2002/0163642 A1 | 11/2002 | Zoval et al. |

* cited by examiner

INTERACTIVE SYSTEM FOR ANALYZING BIOLOGICAL SAMPLES AND PROCESSING RELATED INFORMATION AND THE USE THEREOF

The present application claims priority from U.S. Provisional Patent Application Ser. No. 60/246,824, filed on Nov. 8, 2000, entitled "Interactive Method and System for Analyzing Biological Samples and Processing Related Medical Information Using Specially Prepared Bio-Optical Disc, Optical Disc Drive, and Internet Connections."

TECHNICAL FIELD

The technical field relates generally to diagnostic assays and data processing. In particular, it relates to performing diagnostic assays on an optical disk, processing the test data and distributing the test information across a network.

BACKGROUND

There is an enormous need to make clinical assays faster, cheaper and simpler to perform. One way towards this goal is to simplify the analytical instruments and the testing process so that complex tests can be performed by non-technical employees or even the patients themselves. Another way is to speed-up the diagnostic process by immediately processing the test data and providing the results to authorized individuals who need the information.

Substantial effort has been devoted to miniaturization and integration of various assay operations. Among the newly developed devices are bio-chips and bio-discs. As described in U.S. Pat. No. 6,048,699 to Foley et al., bio-chips are built using silicon chip photolithography techniques, with each chip containing arrays of test sites formed on a substrate. Each of the test sites includes probes therein to bind with target molecules from samples applied to the device, e.g., deposited onto the probes. The binding of a molecule to a probe is noted, thereby identifying the molecule of interest.

Bio-discs are specially designed optical discs that contain all the necessary elements to perform diagnostic assays. Rotation of the bio-disc in a disc drive, such as a CD-ROM/DVD drive, provides a centrifuge capability to prepare and manipulate test samples, and the laser reader in the drive serves as the analytical tool to read the test results. The bio-disc has been described in detail in U.S. Pat. Nos. 5,892,577 and 6,256,088 to Gordon, and U.S. Pat. No. 6,030,581 to Virtanen, which are incorporated herein by reference.

To improve productivity and quality of test data processing, a number of computer-based systems have been developed to analyze and relay medical information. U.S. Pat. No. 5,631,844 to Margrey et al. generally describes a system for simultaneously analyzing medical specimens at remote locations and accessing, for evaluation, the results of each of the analyses at a central laboratory. The system includes a server for storing data in databases and a central laboratory interacting with dedicated computers at each remote locations through the server to analyze the various tests performed on the medical specimens. Interface software is used so that the dedicated computers can interact with the analytical instruments. The system may be used to review, accept or reject test results.

U.S. Pat. No. 6,018,713 to Coli et al. generally describes a network-based system for ordering and reporting medical tests. In this system, computers at the hospitals, laboratories, physicians' and insurers' offices are all inter-connected by a network, such as the Internet. A health care professional may order various tests and retrieve the results of the ordered tests using the system.

U.S. Pat. No. 5,793,969 to Kamentsky et al. describes a network system for reviewing and analyzing computer-encoded microscope slides. Specimens on microscope slides may be scanned using a laser or a video camera. The scanning device is interfaced with an encoding device to record information about the specimen. The digitalized information may be then stored on a network server for analysis.

However, despite these recent advances, there remains a need for a complete assay configuration that combines the simplified assay devices with a data analysis and distribution system so that the diagnostic assays can be performed efficiently and accurately with low cost and rapid turnaround time.

SUMMARY

The present invention combines the bio-disc assay system with computer networking technology to provide an interactive system for analyzing biological, chemical and biochemical agent samples and processing related information. A specially prepared bio-optical disc (referred to as "bio-disc" thereafter) receives a biological sample in a prescribed manner. The sample may include blood, saliva, urine, skin cells, serum, semen, cells from selected body tissue, air samples, bacteria, viruses, fungi, and other biological or chemical material. The bio-disc may include thereon encoded processing software directed to analyzing a biological sample or any number of different biological samples. The bio-disc is then loaded into a bio-disc drive, which is activated by processing software encoded on the bio-disc or by similar software or firmware associated with the hardware or processing circuitry of the bio-disc drive. A reading beam, typically provided by a laser, is used to analyze the biological sample and read the software that may be encoded on the bio-disc. Processing circuitry associated with the bio-disc drive in conjunction with the provided software processes the optical signals received from the biological samples. This processing produces test results, which may be displayed in a desired manner on a video monitor connected to and associated with the bio-disc drive.

In a preferred embodiment, the bio-disc drive, preferably an optical disc read (and write) capable drive, and video monitor may be associated with a computer such as a personal computer in common use today, albeit adapted for safety and environmental concerns. The computer may be connected to a local network and/or the Internet in any one of a number of ways in common practice.

In another preferred embodiment, the present system further includes a remotely located server, which is connected to a local network and/or the Internet. This server may advantageously include processing and control software, which interacts with the software encoded on the bio-disc and/or the software associated with the bio-disc assembly.

In another preferred embodiment, the bio-disc also includes special markings or encoding, such as a serial number, which identifies the bio-disc as an authentic, authorized, or approved bio-disc meeting certain standards. In combination therewith, the processing and control software on the server may be enabled to remotely verify whether the bio-disc is authorized. After authenticity is verified, subsequent processing of the biological sample on the bio-disc is allowed. In the event the control and processing software on the server determines that the bio-disc is not authentic, i. e,. a counterfeit, the control software will prevent processing of the biological sample on the disc. In this manner, a desired level of user security is thus implemented in the system.

In yet another preferred embodiment, the interactive system may be further connected over the internet to doctor's offices, pharmacies, hospitals, emergency care units, ambulances, expert medical systems, and other remote locations such as industrial plants, waste water facilities, food manufacturing and processing sites, military bases, camps and airports, so that the processed medical, environmental or biological warfare information may be dispatched directly thereto for use and/or diagnosis by personnel stationed at such remote locations.

A wide variety of medical information may be generated in this manner. The medical information available from this process may depend on the type of biological sample applied to the disc and the associated processing software which may be encoded on the bio-disc, or associated with the bio-disc drive, or alternatively associated with both the bio-disc and bio-disc drive assembly.

The key advantage of the present invention is that it dramatically simplifies the testing process and makes it more convenient by replacing complex test equipment with an ordinary personal computer and a standard CD-ROM/DVD reader, which is modified for this usage. This enables testing to be done at the point of use. By integrating previously separate steps into a seamless, simplified process, this invention reduces points where errors can occur, provides test results in minutes, speeds the flow of information, allows immediate access to processed data (both current and historical), and expedites the application of appropriate treatment (thereby reducing waste and total system costs). What previously required 5–10 steps and up to 24 hours before a physician received test results now takes two steps and minutes

BRIEF DESCRIPTION OF THE DRAWINGS

The objects, features, and advantages of the present invention are readily apparent from the detailed description of the preferred embodiments set forth below, in conjunction with the accompanying Drawings in which.

DETAILED DESCRIPTION OF THE INVENTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the spirit and scope of the invention. The present invention is not intended to be limited to the embodiments shown, but is to be accorded the widest possible scope consistent with the principles and features disclosed herein.

Figure 1:
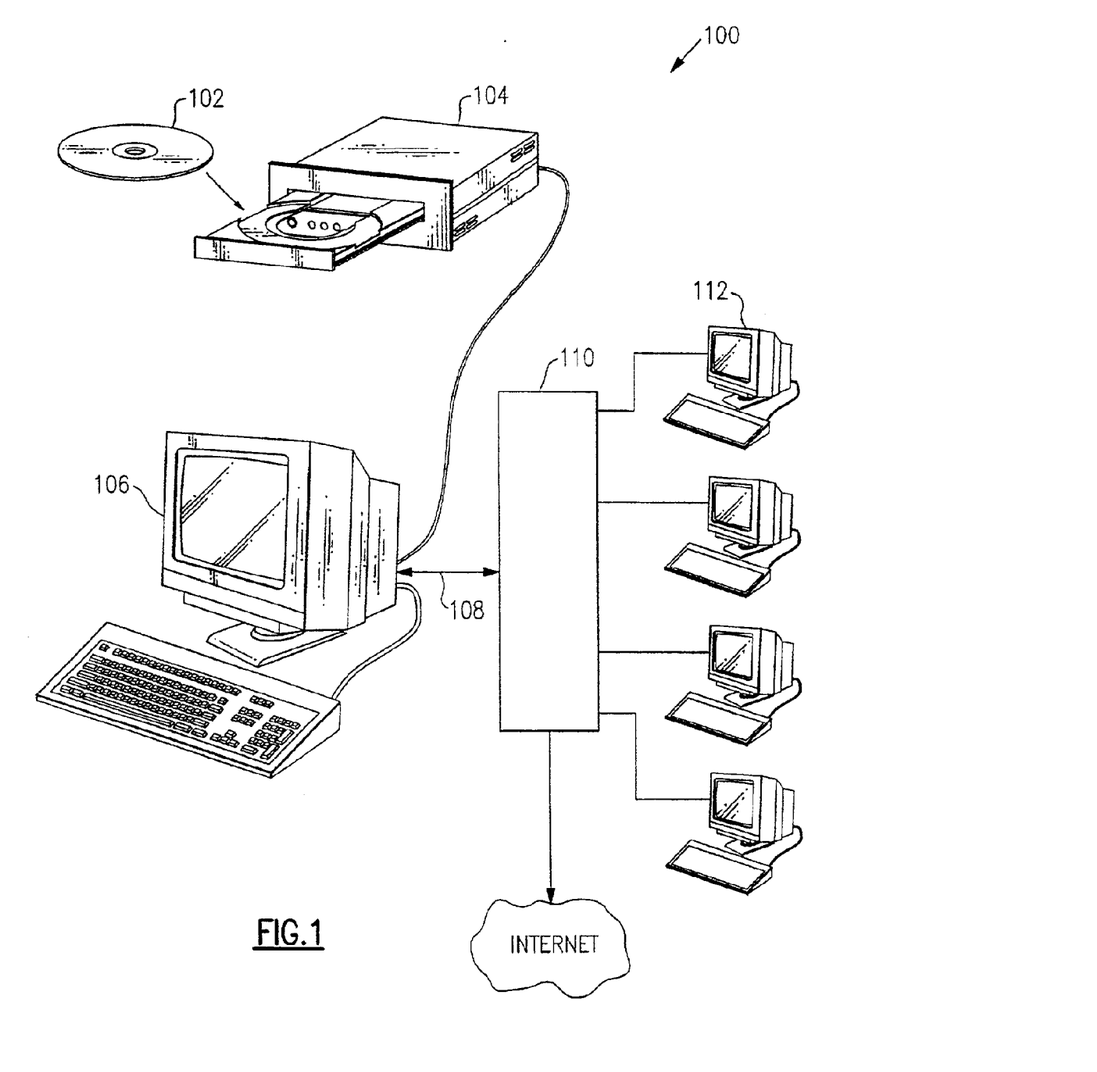
FIG. 1 illustrates a first embodiment of the interactive system of the present invention using bio-discs and a computer to transmit information across a computer network.

FIG. 1 depicts an embodiment of an interactive and remote-controlled system in accordance with the teachings of the present invention and generally designated by the reference numeral 100. As illustrated, interactive system 100 includes specially designed bio-discs 102, a bio-disc drive 104, a computer 106, a connection 108, a server 110, and a number of peripheral terminals 112. The specially designed bio-disc 102 contains assay means to prepare and manipulate test samples, and coded processing information for conducting the assay, the details for which are set forth in U.S. Pat. No. 6,030,581. The bio-disc drive 104 provides dual functions as an analytical tool for performing the assay and as a reader to read and transmit the processing information and test data on the bio-disc 102 and to the computer 106. The computer 106 in this embodiment uses the processing information to convert the raw data into validated test results and send the test results securely and dynamically via the connection 108 to a central data repository server 110, which then forwards the information to authorized individuals at terminals 112. Alternatively, the computer 106 may simply collect and send the raw data to the server for processing. The server 110 may also interact directly with the bio-disc 102 and the bio-disc drive 104 to remotely control the assay process, extract the data, and analyze the result.

In an effort to better understand the nature of the present invention, a short description of the technology involved in the local device, i.e., the computer 106 or like local or field device, as is understood in the art, along with the bio-disc drive 104 reading the bio-discs 102, is provided below.

Figure 2:
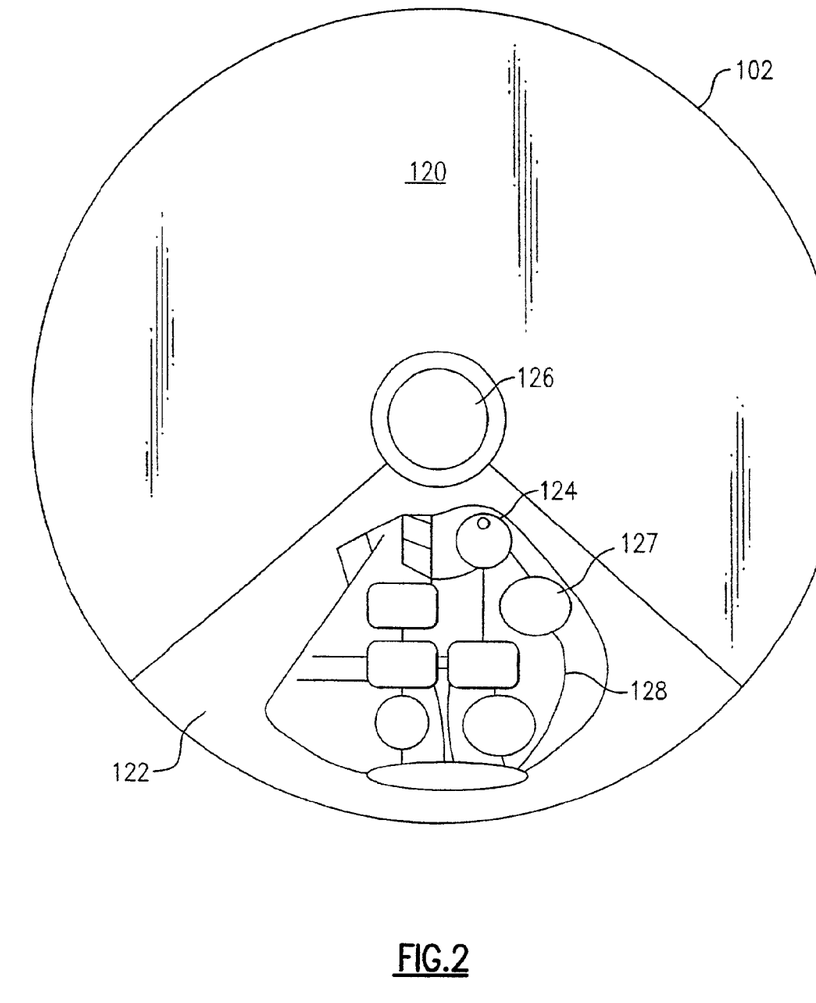
FIG. 2 depicts a general configuration of a bio-disc.

A schematic overall representation of an integrated bio-disc 102 is set forth in FIG. 2. Although the bio-disc 102 may be virtually of any shape and size, for most practical applications the bio-disc is circular having a diameter of 10–1000 mm, most advantageously 20–200 mm and a thickness of 0.1–20 mm, most advantageously 0.5–3 mm. As illustrated in FIG. 2, a bio-disc 102 preferably contains two major sections, a software section 120 and an assay section 122 having a sample inlet port 124 and a number of incubation chambers and microfluidic channels, generally designated by the reference numerals 127 and 128, respectively. A central hole 126 is provided for location in the bio-disc drive 104. Software for controlling the assay may be on a separate disc, the computer 106, the server 110 or else where. However, it is preferred to have the software on the bio-disc 102 associated with an assay for a particular analyte or analytes to minimize the opportunity for human or other error when performing the assay.

Figure 3:
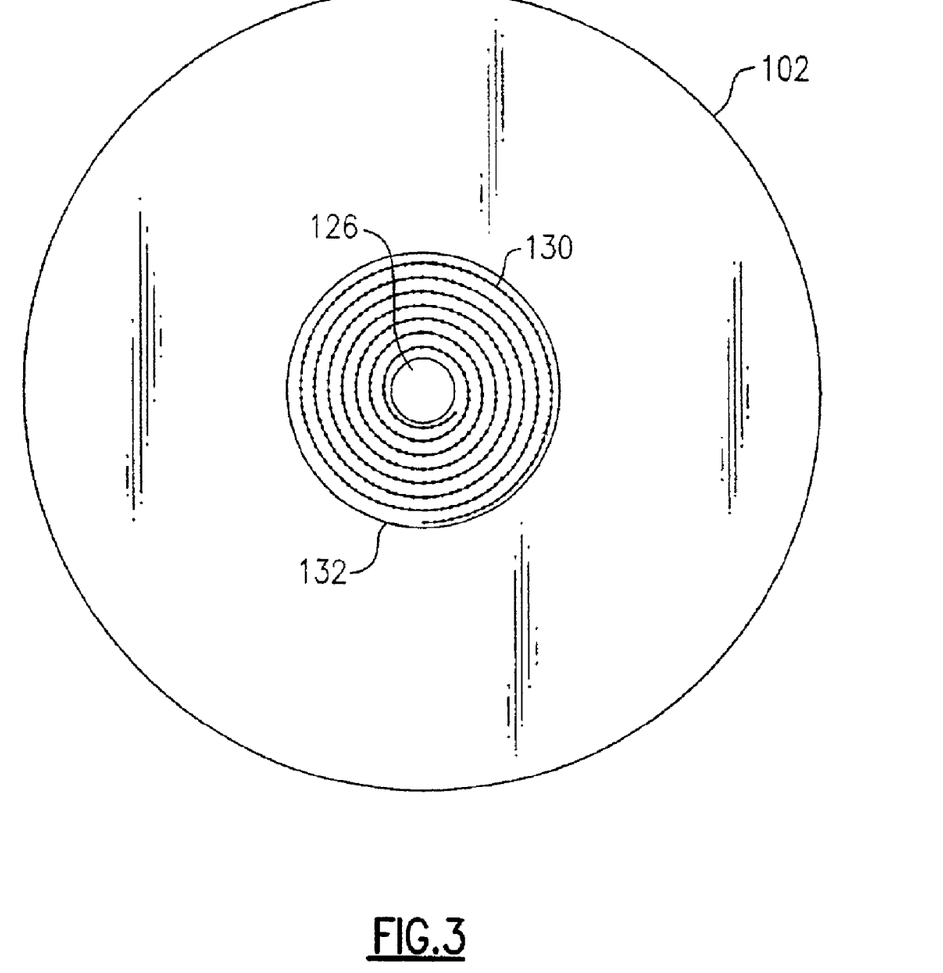
FIG. 3 depicts the bio-disc tracks with bounded test beads as bio-bits.

FIG. 3 depicts an embodiment of a "bio-bit" technology to facilitate signal detection in a bio-disc assay system, which utilizes a number of test beads 130 or other signal elements that are covalently bound to the reflective surface of the bio-disc 102 along disc tracks 132. Each bead 130 on the bio-disc 102 has a specific location or address that allows it to be identified as a bead for a specific test. For example, beads used to detect and quantitate glucose will have addresses different from those used for measuring cholesterol.

Figure 4A:
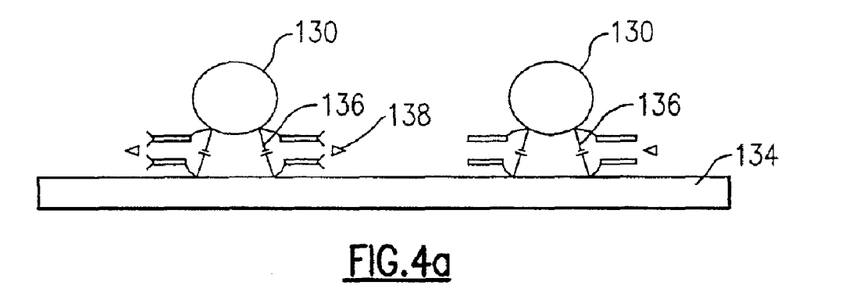
FIGS. 4a–c show the working mechanism of bio-bits.
Figure 4B:
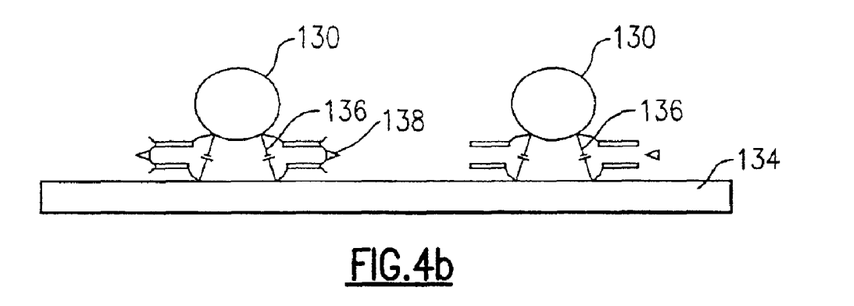
Figure 4C:
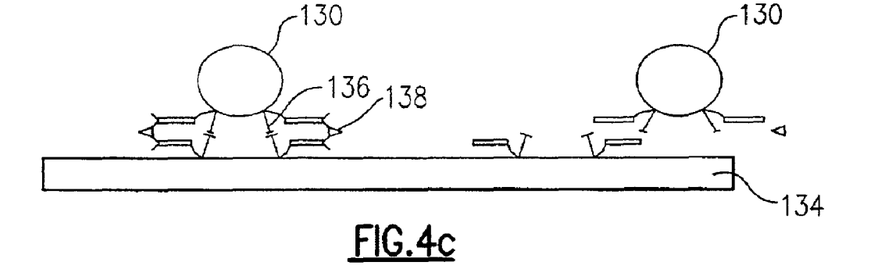

FIGS. 4a–4c demonstrate in more detail a working mechanism of the "bio-bit" technology. In this embodiment, the test beads 130 are attached to the bio-disc surface 134 by linkers 136 (FIG. 4a) that can be cleaved by a wash solution. As shown in FIG. 4b, linker 136 may be engineered to bind specific analytes 138, which in turn results in the formation of additional linkages between the test bead 130 and the disc surface 134. The test beads 130 are then washed with the wash solution which cleaves linker 136 and releases the test beads 130 from the disc surface 134. The test beads 130 that remain on the surface after the washing step are specific to the desired analyte 138 and directly proportional to the amount of analyte 138 present in the test sample (FIG. 4c). A more detailed description about the aforementioned bio-bit technology can be found in Applicants' assignee's co-pending patent application, entitled "Signal Processing Apparatus and Methods for Obtaining Signal Signatures of Investigational Features Detected on a Surface of an Optical Disc Assembly," U.S. Provisional Patent Application Ser. Nos. 60/270,095 and 60/292,108, filed on Feb. 20, 2001 and May 18, 2001, respectively, which are incorporated herein by reference.

The bio-disc 102 may also be used to detect and quantify cells. One approach is to attach antibodies to specific cell surface molecules on both the test beads 130 and disc surface 134. This allows the test beads 130 to remain attached to the disc surface 134 in response to the presence of specific cells. Another approach is to use laser signals that are distorted by the attached cells to map the topology of the cell. This approach potentially allows the mapping of internal organelles of a cell, such as the nucleus.

Figure 5:
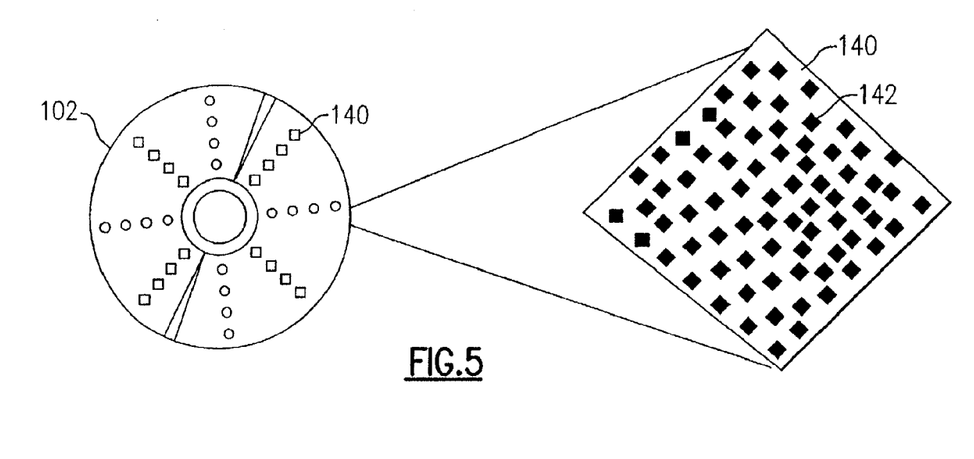
FIG. 5 depicts an "open-disc" configuration of a bio-disc.

FIG. 5 depicts an open-disc configuration for simple bioassays where groups of tests may be located in a specific hydrophilic sample location 140 on the bio-disc 102 that is exposed to one sample. Each bio-disc 102 may support up to 100 sample locations 140. Each sample location 140 may contain as many as fifty separate tests 142. An example of an open-disc configuration can be found in Applicants' assignee's co-pending patent application entitled "Surface Assembly for Imbolizing DNA Capture Probes and Bead-Based Assay Including Optical Bio-Discs and Methods Relating Thereto," U.S. Provisional Patent Application Ser. No. 60/257,705, filed on Dec. 22, 2000, which is incorporated herein by reference.

Figure 6:
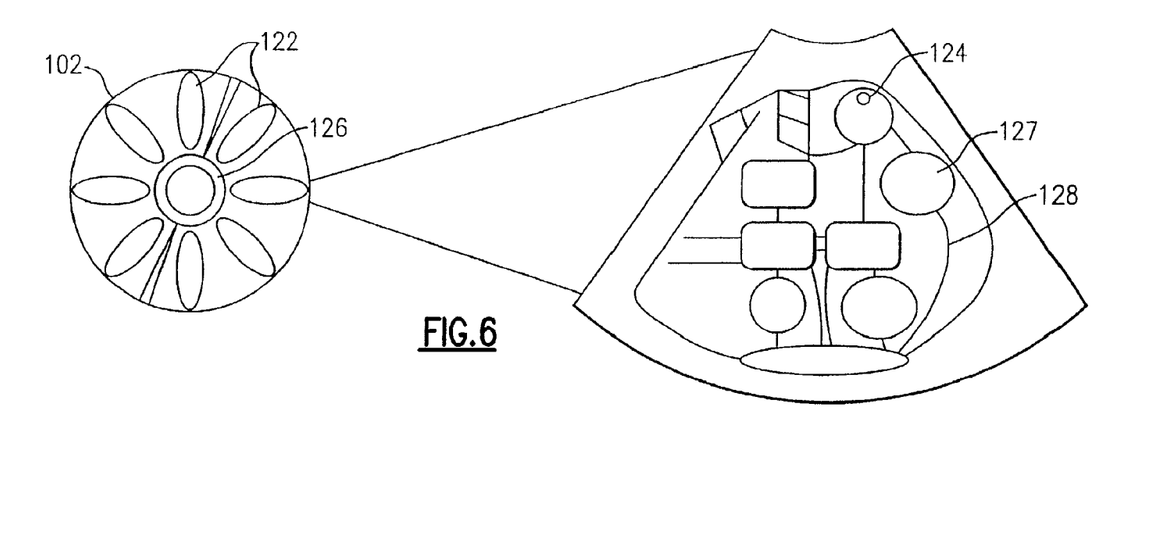
FIG. 6 depicts a "lab-in-a-disc" configuration of a bio-disc.

FIG. 6 depicts a lab-on-disc configuration for more complicated assays. The bio-disc 102 may be configured to have multiple assay sections 122. Each assay section 122 is capable of performing multiple tests. A single bio-disc 102 may have as many as 30 assay sections 122, with up to 20 different test per assay section. As noted, the sample inlet port 124 allows insertion of a sample into the various incubation chambers 127 and processing via the manipulation of the various microfluidic channels 128, as illustrated. A more detailed description about the lab-on-disk configuration can be found in U.S. Pat. No. 6,030,581 to Virtanen, which is incorporated herein by reference.

As is known in this art, the bio-disc 102 may rotate up to 16,000 rpm in conventional CD-ROM or DVD drives. In all CD-ROM and DVD drives the speed is adjustable within certain limits (200–16,000 rpm). However, for some operations it may be advantageous to utilize rotations at differing speeds, for example 1000–10,000 rpm, and most preferably 2000–5000 rpm. For any particular assay, the processing software dictates the rotation regimen during the analysis. This regimen, the speeds and timing, including times in which perhaps no rotation occurs to allow for incubation, electrophoresis, isoelectric focusing, etc., is controlled to deliver reagents and sample to appropriate sites on the assay sector 122 as dictated by the assay protocols. Available rotational speeds do allow for a significant centrifugal force that may be used to move liquids.

The laser reader in a conventional CD-ROM or DVD drive (or modified version thereof discussed hereinbelow) may also be used as an energy source to heat samples or maintain samples at a desired temperature. Another energy source that may be easily used in the bio-disc is chemical energy. A most suitable form of chemical energy is released by a battery in the form of electrical energy. Mechanical and chemical energy allow the operation of many kinds of components. Important components of a bio-disc may include one or more of the following: capillaries, containers, filters, dialysis membranes, chromatographic columns, electrophoretic gels, valves, any micromechanical or electronic components including microprocessors, electrodes, especially enzyme electrodes, cuvettes, and assay elements. The possible unit operations carried out by the components include the following: centrifugation, filtering, transfer of liquids, mixing of liquids, dialysis, column separations, heating, cooling, electroconvection, electrophoresis, and analyte detection and signaling thereof.

The bio-disc drive 104 may be a standard CD-ROM/DVD drive with a reader laser to detect the presence or absence of signal elements (e.g. the aforementioned test beads 130) attached to the disc surface. With audio, video or data discs, the laser is able to detect changes in surface reflectivity of a disc when the surface is modified to carry digital audio or video signals. Similarly, with the bio-disc, the laser detects the presence of a test bead 130 on the bio-disc surface that blocks part of the laser light normally reflected to the reader detector. Test beads have characteristic reflective signatures, which allow them to be differentiated from surface contaminants, such as dust or salts that may bind to the disc surface during a test reaction.

When testing is performed using the open-disc configuration, standard CD-ROM/DVD drives may also be incorporated into a robotic disc processor. The disc processor performs all of the functions necessary to analyze up to 300 samples per hour, such as pipetting sample, adding reagents, mixing, washing, incubation, disc movement, analysis, result calculation, data recording and transmission. The disc processor allows for high volume, walk-away testing at larger central laboratories. However, in spite of the robotic features added to enable high volume testing, the analysis is still performed with an inexpensive, commercially available disc drive reader, making the overall process very cost efficient.

Using the software included on each bio-disc, the computer 106 attached to the drive 104 acts to analyze, interpret, and store test results. The analytic data and results may be stored on the computer hard drive or transmitted through connection 108 to a server 110 for further processing, as discussed hereinabove and a further detail hereinbelow.

The software included with each bio-disc uses digital signals supported by specially designed algorithms to interpret and transmit test data via connection 108 to the server 110. The transmission is preferably through a secured path.

The connection 108 may be the Internet or a local network. The server 110 serves as a central data repository that will aggregate test data and facilitate statistical analyses, such as trending and multivariate analyses, as well as pattern recognition analyses. Test results may also be transmitted from the server 110 to authorized individuals who require the information at terminals 112. Examples of the authorized individuals include physicians and care managers for the healthcare market, product development and quality management departments of food manufacturing companies in the food processing market, and military command and government agencies for the military and public safety market. A more detailed description of software employed in practicing the system and methodology of the present invention may be found in Applicants' assignee's co-pending patent application entitled "Variably Sampling Control for Rendering Pixelation of Analysis Results in Optical Bio-disc Assembly and Apparatus Relating Thereto," U.S. Provisional Patent Application Ser. No. 60/291,233, filed May 16, 2001, which is incorporated herein by reference.

The bio-disc 102 may also include special markings or encoding, such as a serial number, which identifies the bio-disc 102 as an authentic, authorized, or approved bio-disc meeting certain standards. In combination therewith, the processing and control software on the server 110 may be enabled to remotely verify whether the bio-disc is authorized. After authenticity is verified, subsequent processing of the biological sample on the bio-disc is allowed. In the event the control and processing software on the server determines that the bio-disc is not authentic, i.e. a counterfeit, the control software will prevent processing of the biological sample on the bio-disc 102. In this manner, a desired level of user security is thus implemented in the system 100. A more detailed description of the discs employed in the instant invention and a variety of uses thereof may be found in Applicants' assignee's co-pending patent application entitled "Trackable Optical Discs With Concurrently Readable Analyte Material," International Application No.PCT/US99/25136, International Filing Date Oct. 26, 1999.

The interactive system 100 may be further connected over the Internet to doctor's offices, pharmacies, hospitals, emergency care units, ambulances, expert medical systems, and other remote locations so that the processed medical information may be dispatched thereto for use and/or diagnosis by personnel stationed at such remote locations.

Figure 7:
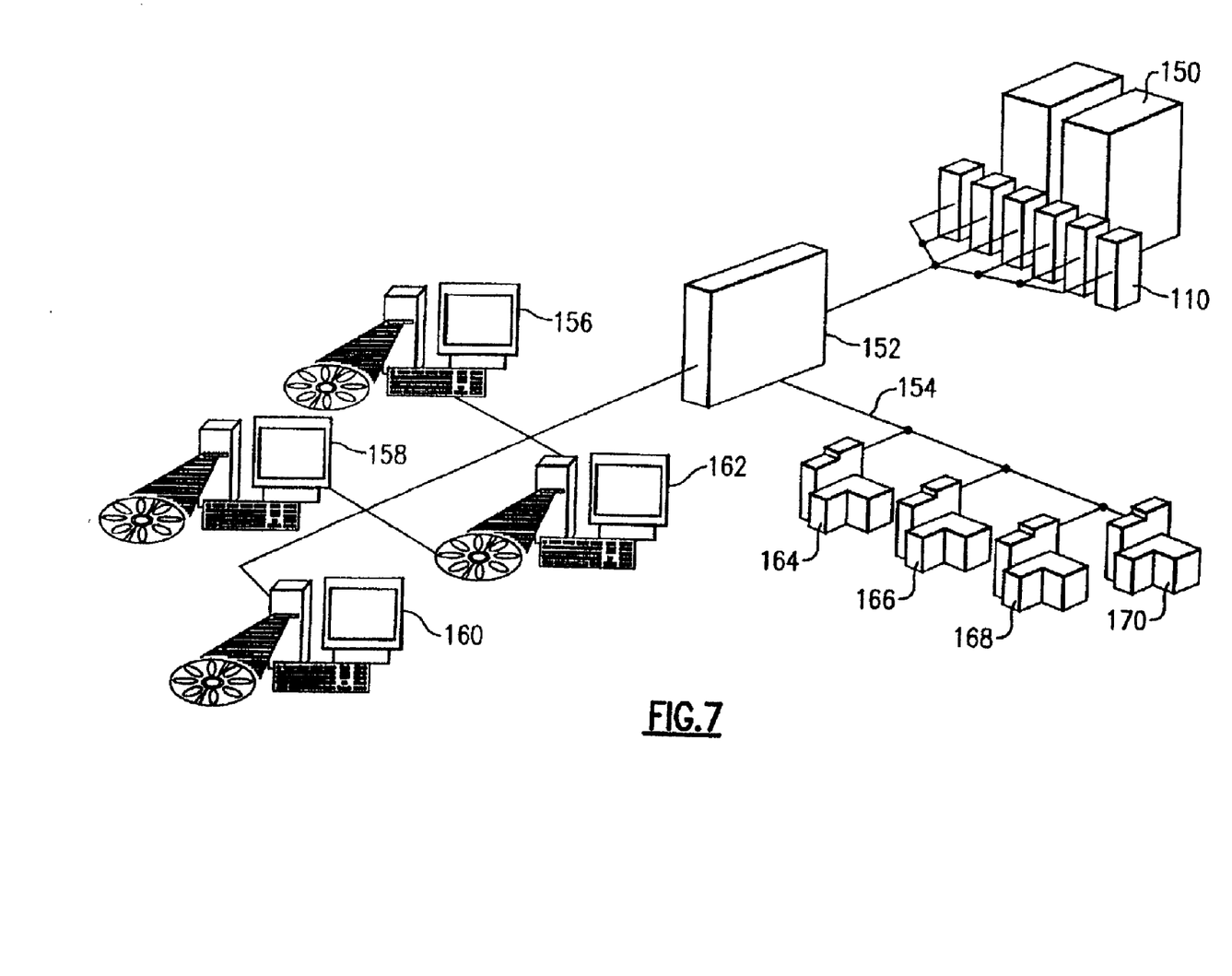
FIG. 7 shows the integration of the interactive system with the Internet.

As shown in FIG. 7, the bio-disc system may integrated with the Internet to transmit results to authorized individuals needing the information and to upload test results to a central data repository, generally designated by the reference numeral 150. As a result, it is possible to aggregate data in a way not currently possible; through data mining and analyses at the aforementioned server 110, which is in communication with the central data repository 150 and which may also serve as a data center, new information may be collected and displayed on a website 152 to help customers or the central data repository 150 meet their specific needs better, faster, and more inexpensively.

The Internet (illustrated by the reference numeral 154) interconnects the central data repository 150 and the website to a variety of disparate nodes, e.g., doctor's offices, hospitals and like facilities in one embodiment directed to marketing test units to these facilities, and generally designated in FIG. 7 by the reference numeral 156. In another embodiment, directed to marketing home test units, also designated by the reference numeral 156, patents input samples into their home test unit. In both embodiments, the test units 156, test the samples, forwards the data resultant therefrom, and is able to receive commands or other information or test interpretation, treatment, response options, relevant products, etc., as pertaining to that sample from a remote device. Physicians, patients and/or care managers located at another facility 164, also are notified of the test results and act on it. Similarly, industrial plants and waste water facilities 158, food manufacturing and processing sites 160, and military bases, camps and airports 162 input test results to respective other facilities, as illustrated in FIG. 7, including food product development, marketing and safety department 166, the Environmental Protection Agency (EPA) or Occupational Safety and Health Administration (OSHA) 168, and a military, airport or public security command 170.

The present invention therefore dramatically reduces the need for expensive instrumentation and technical staff. Existing testing instruments cost $10,000 to $400,000, and perform a limited number of test classes. Many are not as sensitive or as accurate as the bio-disc system; all are much more expensive than the bio-disc system. The highly advanced, yet simple-to-use and inexpensive bio-disc technology platform of the present invention provides a very cost effective way to perform many types of tests: clinical laboratory tests, such as immunoassay, cell analysis, inorganics, small molecules, and nucleic acid-diagnostics; food tests, such as *E. coli* and *Salmonella*; waste water tests to detect the presence of contaminants, such as bacteria, lead, and mercury; agriculture tests, such as potassium and phosphate; environmental testing of the air for pollution or other airborne particulates, particularly chemical and biological contaminates, including spores, bacteria, viruses, fungi and toxic substances; and chemical and biological warfare agent detection, such as the presence of Anthrax, small pox and brucella.

Further, by integrating previously separate steps into a seamless, simplified process, the present invention reduces points where errors can occur, speeds the flow of information, allows immediate access to processed data (both current and historical), and helps to create new, value-added information. The bio-disc technology supports a reduction in total "system" costs by providing test results in minutes, reducing errors, and expediting the application of appropriate treatment (thus reducing waste).

Figure 8:
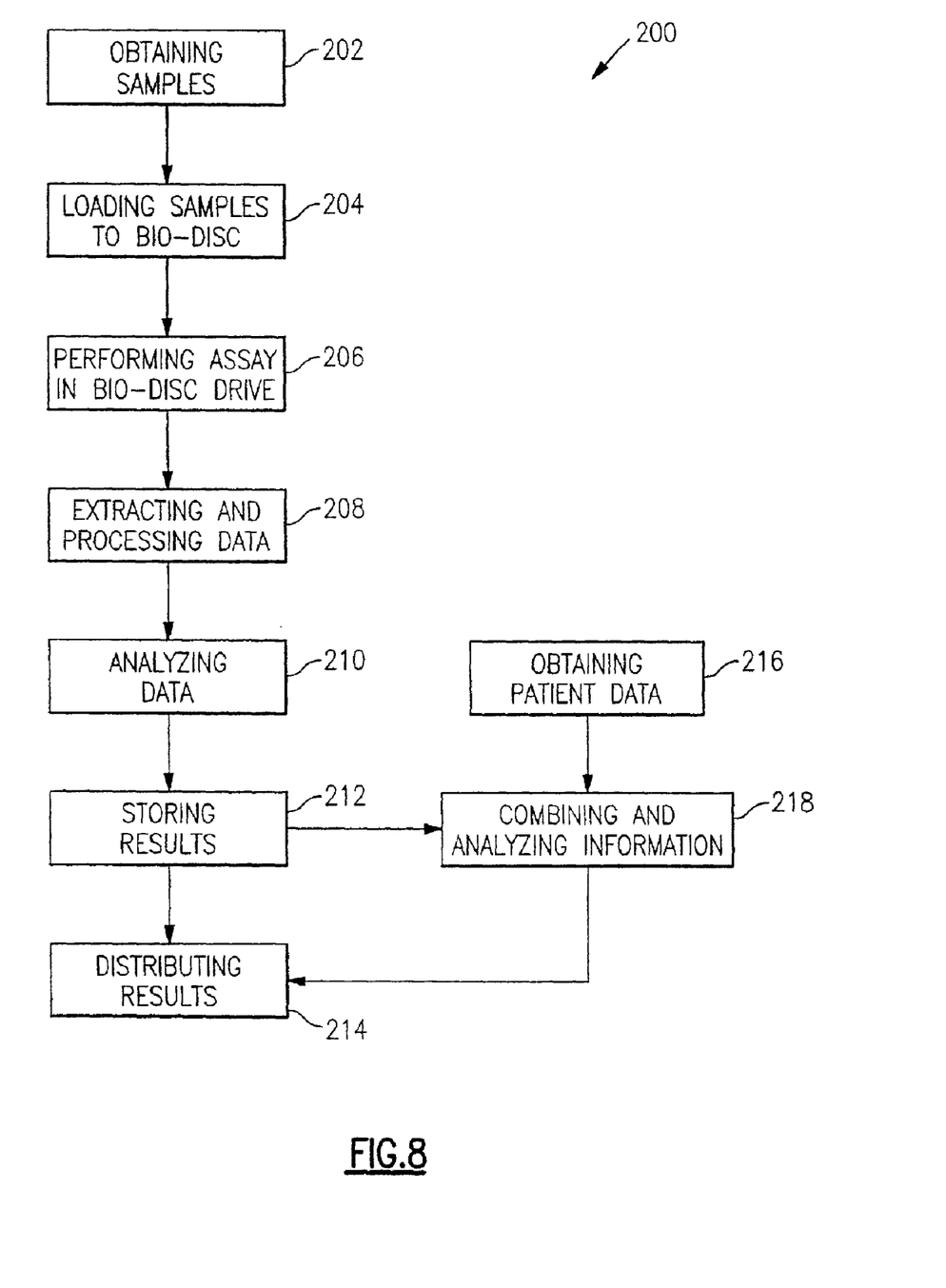
FIG. 8 depicts a method for using the interactive system.

FIG. 8 illustrates an embodiment of a methodology, generally designated by the reference numeral 200, for analyzing biological samples with the aforedescribed interactive system 100. The method 200 includes the following steps: obtaining biological samples from patients or other source (202); loading the samples onto the bio-disc (204) which may be performed manually or mechanically; performing diagnostic tests in a bio-disc drive (206); collecting and processing test data by a local computer or a central server (208); analyzing test data in the central server (210); storing test results in the central server (212); and distributing the test results through a network to authorized users (214). Optionally, other patient information, such as health history and genetic make-up, may be obtained (216), combined with the test results and analyzed to generate new information (218) to be distributed through the network to the authorized users (214). Additional steps, such as a step to authenticate the bio-disc used in step 204, and a step to check the user authorization, may also be added to provide a desired level of user security.

As discussed above, the present invention is directed to test units placed in a health care provider environment such as doctor's offices, hospitals, nursing houses, and other such facilities, and to test units placed in user's homes. As such, the invention may be marketed to the users directly. Additionally, the contexts of the usage may be controlled, such as in an intranet or other proprietary network. In instances where non-proprietary data transmission mechanisms are employed, e.g., the Internet and wireless communications, additional security and identification features may be required to preserve confidentiality. Additionally, where public health and safety are concerned, governmental or private industry concerns may monitor the environment by placing the detection kits of the instant invention in a variety of public areas, e.g., a subway station, to monitor for toxins or other agents harmful to the welfare of the populace.

Figure 9:
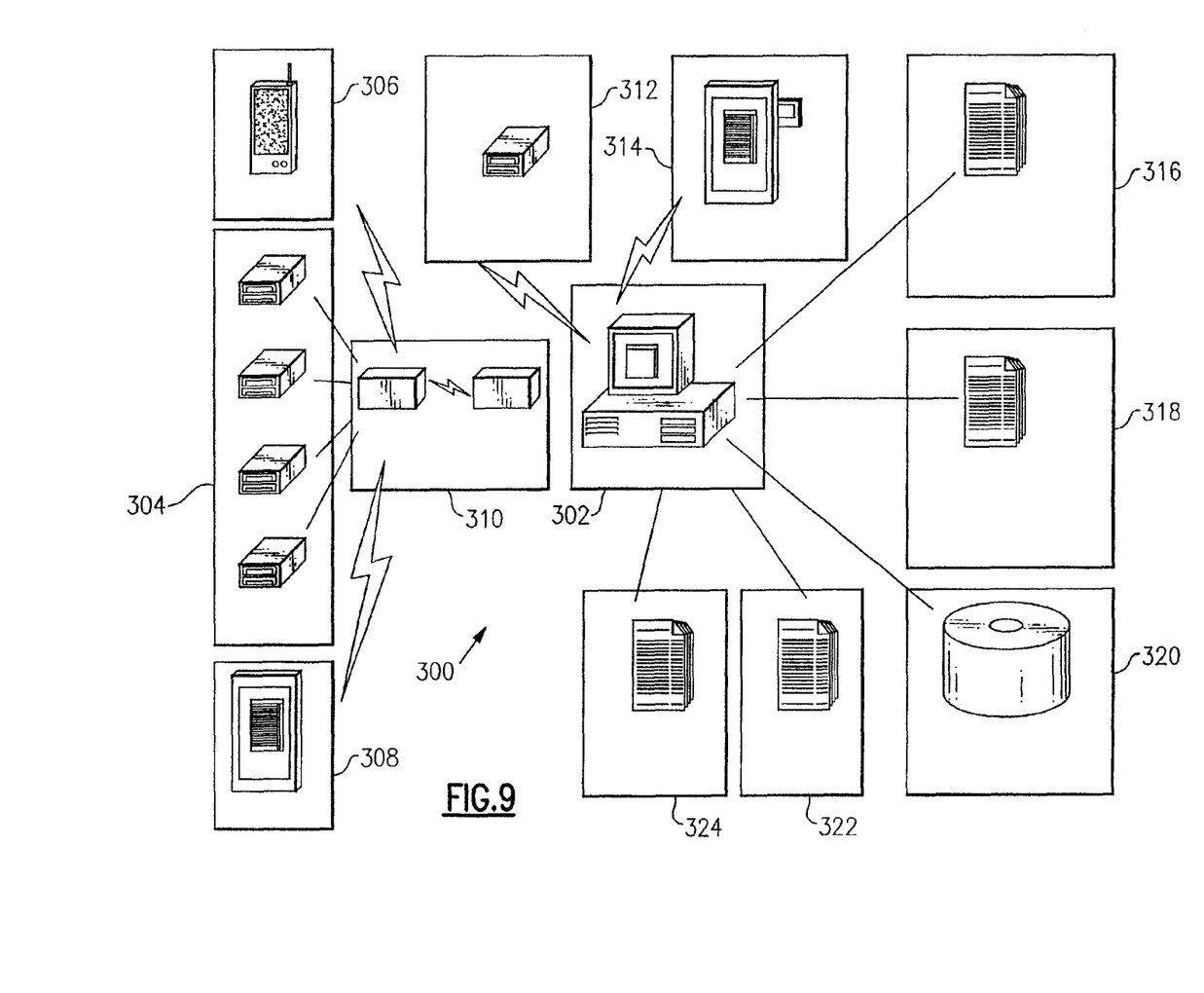
FIG. 9 illustrates another embodiment of the interactive system of the present invention.

With reference now to FIG. 9 of the drawings, another embodiment pursuant to the teachings of the present invention, generally disignated by the reference numeral 300 is illustrated. A central management system 302 in this embodiment communicates with a variety of peripheral or remote devices, e.g., bio-disc devices 304 connected directly, wireless PDAs 306 and wireless tablets 308 connected wirelessly, to a TCP/IP and VPN device 310, which, in turn, communicates directly to the central management system 302, as illustrated. Similarly, ambulatory field bio-disc analyzers 312 and wireless field bio-disc analyzers 314 may be wirelessly in communication with the central management system 302. Administratively, the central management system 302 is also in communication with a reimbursement system 316, a patient billing and accounting interface 318, a patient records database 320, a point of contact (POC) EDI for transactions 322 and a report generator 324.

As discussed hereinabove, the principles of the present invention are applicable in a variety of contexts, e.g., doctor's offices and home test kits, and employing a variety of technologies, only a few of which are discussed herein and enumerated below. The networks employed may be an intranet or private network having inherent security and communications protocols or an internet, such as the Internet, with the appropriate firewalls requiring identification, e.g., passwords, barcodes, biometrics or other identification means.

A variety of communication protocols may be employed, including TCP and TCP/IP connections of packatized communications, UDP connections, IPX/SPX networking protocols, cellular connections, wireless connections, and infrared interfaces to interconnect disparate devices, e.g., using Bluetooth. Indeed, the medical data being transmitted across a network may also be encrypted across these connections to provide the requisite security in transmission, as is understood to those of skill in the art.

The medical data collected from the spinning translucent/transparent bio-discs may be employed for purposes of medical diagnostics, research, detection systems, and aggregation for demographics or other data mining purposes, e.g., in OLAP server/client uses, spreadsheets, graphical displays and printouts. The medical data gathered from the optical discs of the present invention, e.g., CD/CDR/CDRW/DVD bio-discs, may be displayed from data gathered in a variety of formats, including standard text, HTML, Java, ActiveX, various proprietary TCP/IP display protocols, proprietary network-based protocols and encrypted methods, e.g, IIS, 56 bit and 128 bit methods, as are understood to those of skill in the arts.

It should also be understood that the control of diagnostic devices may be effectuated via web-based control, HTTP, Java and a variety of proprietary applications. In other words, a remote device may communicate with and control a local device actually performing the sample measurements, permitting centralized control of a number of users, whether doctor's or clinic's offices or by a user themselves employing a home test kit. By virtue of such remote control, the local user is prevented or thwarted from copying the local device or otherwise subverting the process.

One particular use of the principles of the present invention is in the utilization of use or application for the purpose of reimbursement in an automated fashion from a healthcare provider and/or coverage system, including but not limited to Medicare, Blue Cross or like providers.

It should further be understood that the present invention may also be employed to remotely review and manipulate the locally-produced devices or instruments, as well as the medical data collected therefrom. For example, via the above or other communications protocols, a remote user may calibrate the locally-stored software, providing a software update or patch for the bio-disc or associated instrumentality, perhaps expanding the capabilities of the bio-disc or components connected thereto, as a host device connects to and communicates with a field device. Likewise, control and testing of the bio-disc and components may be done remotely via the variety of communications protocols set forth hereinabove. Similarly, data obtained by the bio-disc and components may be recalculated and compared.

When using the Internet for communications, the present invention is also directed to methodologies to fully exploit advantages afforded the Internet, e.g., the ability to assign a static Internet Protocol (IP) address and the ability to assign a system to use dynamic assignment of Internet addresses, e.g., DHCP, to obtain an address to gain access to networking capabilities. Similarly, the present invention is directed to techniques to utilize a gateway address entry and/or DNS addresses in order to obtain network capabilities.

It should also be understood that a variety of data may be manipulated pursuant to the teachings of the present invention. For example, the raw, unprocessed data collected by a bio-disc may be sent across the network to a remote device for processing, providing the most control to a provider of these services. Conversely, a local device may process the data and forward result data to the remote device across a private or public network, providing the most control to the user of the services. In between are situations where the local and remote (and potential intermediary) devices share or compartmentalize the calculations, e.g., the remote device authorizing or enabling the respective local device (or devices), initiating the processing, coordinating the processing and transmitting the results therefrom.

Similarly, remote device access of local or field devices via a network conversion may be employed for purposes of remote control, operation and data access for problem identification, problem resolution, troubleshooting, data aggregation, product ordering and a variety of other like functionalities. Furthermore, the accessing, directing, upgrading, data collection and data analysis may be performed at or by clinical labs, physicians, hospitals, clinics, mobile devices, individual personal use, scientific laboratories, and remote access research, including devices utilizing satellites for remote research devices either in high altitudes or mountains or desolate areas, and under the surface of the earth or water in research vessels.

It should be understood to those skilled in the art that the equipment employed in analyzing the various biological samples, some of which could be quite hazardous, would include various safety and environmental features not found in standard CD-ROM and DVD devices, such as found in the home. The various additional features are necessary to guard the integrity of the devices themselves, e.g., from centrifuged particulates damaging the mechanism, and from biohazards under analysis escaping into the surrounding environment. The requisite modifications and adaptations to the equipment and the requisite software therefore are discussed hereinabove and in the aforementioned co-pending applications.

It should further be understood that the optical disc technology of the present invention, although currently deployed in the shape of compact diskettes, may be employed in a variety of other configurations, including non-circular discs and a variety of geometrical shapes as may be useful in the art, e.g., cylinders or spheres or other shapes amenable to centrifugal forces.

Although preferred embodiments and their advantages have been described in detail, various changes, substitutions and alterations can be made herein without departing from the spirit and scope of the sintering process as defined by the appended claims and their equivalents.

What is claimed is:

1. An interactive testing system for analyzing biological, chemical and biochemical samples, comprising:
    a bio-disc including bio-disc authentication information, said bio-disc adapted to receive a sample;
    a bio-disc drive adapted to process said bio-disc and retrieve information from said sample;
    a central processing unit for controlling said bio-disc drive;
    means for allowing said central processing unit to communicate over a network; and
    a node connected with said network, said node being enabled to interact with said central processing unit and said node configured to evaluate the bio-disc authentication information so as to verify authenticity of the bio-disc.

2. The interactive testing system according to claim 1, wherein said node is implemented so that processing and analysis of said sample is remotely controlled.

3. The interactive testing system according to claim 1, wherein said bio-disc comprises processing software encoded thereon.

4. The interactive testing system according to claim 3, wherein said processing software encoded on said bio-disc is operable after said node verifies authenticity of said bio-disc.

5. The interactive testing system according to claim 1, wherein the node comprises a server.

6. The interactive testing system according to claim 1, further comprising a user terminal connected to the node.

7. A method for analyzing biological, chemical and biochemical samples comprising:
    obtaining a sample;
    loading the sample to a bio-disc;
    obtaining bio-disc authentication information from the bio-disc;
    performing a test on said sample on said bio-disc in a bio-disc drive;
    collecting test data on said sample by a reader;
    processing the test data by a computer in communication with said reader;
    transmitting processed test data from said sample to a server;
    transmitting bio-disc authentication information to the server;
    authenticating the bio-disc information at the server; and
    obtaining a test result from the server.

8. The method of claim 7, further comprising the steps of:
    obtaining information related to said sample;
    transmitting the sample-related information to the server;
    obtaining a test result analysis from the server based on the test result and the sample-related information.

9. The method of claim 8, wherein the sample-related information is health information from a patient from whom the sample is taken.

10. A method for analyzing biological, chemical and biochemical samples, said method comprising the steps of:
    receiving test data from a remote location, said test data being generated from a sample using a bio-disc and processed by a computer at the remote location;
    analyzing the test data to produce a test result;
    storing the test result in a server accessible by authorized users
    obtaining bio-disc authentication information from the remote location;
    authenticating the bio-disc information; and
    subsequent to bio-disc authentication, permitting access to the stored test results by authorized users.

11. The method of claim 10, further comprising the step of:
    receiving health information of a patient from whom the sample is taken;
    storing the test result and the health information into a central data base;
    extracting and analyzing information related to the test result and the health information from the data base to produce a test result analysis; and
    storing the test result analysis on the server accessible by authorized users.

12. The method of claim 10, wherein the test result in the central server is accessible through a web page.

13. A method for analyzing biological, chemical and biochemical samples, comprising the steps of:
    obtaining test data from a remote location through a network;
    analyzing the test data on a server to produce a test result; and
    storing the test result in the server, said server accessible by authorized users,
    wherein the test data is generated by processing a sample in a bio-disc with a bio-disc drive;
    authenticating bio-disc information contained on the bio-disc; and
    subsequent to bio-disc authentication, permitting access to the stored test results by authorized users.

14. The method of claim 13, wherein the network is the Internet and the server is accessible through a web page.

15. The method of claim 13, further comprising the steps of:
    receiving test related information;
    storing the test result and the test related information into a central database;
    extracting and analyzing information related to the test result and the test related information from the central database to produce a test result analysis; and
    storing the test result analysis on the server accessible by authorized users.

16. An interactive testing system for testing samples, said testing system comprising:
- a bio-disc device including bio-disc authentication information and containing means thereon for analyzing a sample and generating a plurality of test data therefrom;
- a local device connected to said bio-disc device and receiving said plurality of test data from said bio-disc device; and
- a remote device connected to said local device across a network, said plurality of test data being sent from said local device to said remote device across said network, said remote device processing said plurality of test data upon receipt and said remote device configured to evaluate the bio-disc authentication information so as to verify authenticity of the bio-disc and subsequent to said verification, to permit authorized user access to said processed test data.

17. The interactive testing system according to claim 16, wherein said local device further comprises means for processing said plurality of test data.

18. The interactive testing system according to claim 17, wherein said local device processes said plurality of test data after receipt of a processing signal from said remote device.

19. The interactive testing system according to claim 18, wherein said processing signal from said remote device, upon receipt at said local device, enables the processing of said plurality of test data by said local device.

20. The testing system according to claim 16, wherein said local device is located in a medical office and remotely accessible by said remote device, the processing of said plurality of test data at said local device being enabled by the remote device.

21. The interactive testing system according to claim 20, wherein the processing of said test data at said local device is coordinated by said remote device.

22. The interactive testing system according to claim 16, wherein said local device is located in a user's home and remotely accessible by said remote device, the processing of said plurality of test data of said local device being enabled by the remote device.

23. The interactive testing system according to claim 16, wherein said local device is a field device remotely accessible by the remote device.

24. The interactive testing system according to claim 16, wherein said local device is in wireless communication with said remote device.

25. The interactive testing system according to claim 16, wherein said plurality of test data sent across said network is encrypted.

26. The interactive testing system according to claim 16, wherein said network is an intranet.

27. The interactive testing system according to claim 16, wherein said network is the Internet.

28. The interactive testing system according to claim 16, wherein said network employs a connection selected from the group consisting of: a TCP connection, a TCP/IP connection, a UDP connection, a cellular connection, a wireless connection, an infrared connection, and an IPX/SPX networking connection.

29. The interactive testing system according to claim 16, where said local device is in communication with said remote device via the Internet, said communication employing an Internet address.

30. A method for analyzing biological, chemical and biochemical samples, said method comprising the steps of:
- receiving test data from a remote location, said test data being generated from a sample using a bio-disc and processed by a computer at the remote location;
- analyzing the test data to produce a test result;
- storing the test result in a server accessible by authorized users;
- obtaining bio-disc authentication information from the remote location;
- authenticating the bio-disc information; and
- subsequent to bio-disc authentication, accessing the test result in the server through a web page.

* * * * *